(12) United States Patent
Hänsel

(10) Patent No.: US 6,478,792 B1
(45) Date of Patent: Nov. 12, 2002

(54) METHOD AND APPARATUS FOR ILLUMINATION OF THE EYE

(75) Inventor: Harmut G. Hänsel, Ilmnitz (DE)

(73) Assignee: Carl Zeiss Jena GmbH, Jena (DE)

( * ) Notice: Subject to any disclaimer, the term of this patent is extended or adjusted under 35 U.S.C. 154(b) by 125 days.

(21) Appl. No.: 09/654,056

(22) Filed: Sep. 1, 2000

Related U.S. Application Data

(60) Provisional application No. 60/152,271, filed on Sep. 3, 1999.

(30) Foreign Application Priority Data

Sep. 3, 1999 (DE) .......................... 199 43 723
Sep. 3, 1999 (DE) .......................... 199 43 735

(51) Int. Cl.$^7$ .............................................. A61B 18/18
(52) U.S. Cl. ................................................. 606/5
(58) Field of Search ................... 351/205, 206; 606/4, 5, 6; 623/6.11, 6.12

(56) References Cited

U.S. PATENT DOCUMENTS

| | | |
|---|---|---|
| 4,718,418 A | 1/1988 | L'Esperance, Jr. |
| 4,941,093 A | 7/1990 | Marshall et al. |
| 5,133,748 A * | 7/1992 | Feaster ............... 623/6.12 |
| 5,246,435 A * | 9/1993 | Bille et al. ............ 606/6 |
| 5,334,190 A | 8/1994 | Seiler |
| 5,423,801 A | 6/1995 | Marshall et al. |
| 5,505,723 A | 4/1996 | Muller |
| 5,520,679 A | 5/1996 | Lin |
| 5,549,632 A | 8/1996 | Lai |
| 5,613,965 A | 3/1997 | Muller |
| 5,624,436 A | 4/1997 | Nakamura et al. |
| 5,637,109 A | 6/1997 | Sumiya |
| 5,651,784 A | 7/1997 | Klopotek |
| 5,711,762 A | 1/1998 | Trokel |
| 5,713,892 A | 2/1998 | Shimmick |
| 5,735,843 A | 4/1998 | Trokel |
| 5,740,803 A | 4/1998 | Gray et al. |
| 5,807,379 A | 9/1998 | L'Esperance, Jr. |

FOREIGN PATENT DOCUMENTS

| | | |
|---|---|---|
| DE | 4131361 C2 | 3/1993 |
| DE | 19752949 A1 | 6/1998 |
| EP | 0657151 A1 | 6/1995 |
| WO | WO 9819741 | 5/1998 |

* cited by examiner

Primary Examiner—George Manuel
(74) Attorney, Agent, or Firm—Birch, Stewart, Kolasch & Birch, LLP

(57) ABSTRACT

A method and a device for irradiation of the eye can be used in opthamology, refractive surgery and laser medicine. It combines the working principles of specific optical and electronic modules to expose the eye lens to controlled therapeutic radiation in the long-wave UV-A range above cornea absorption and/or the visible and/or the near infra-red ranges and/or the cornea in a defined way to treatment radiation in the near infra-red wavelength range about 1.3 micrometers, whereby locally photo-induced irreversible chemical changes are created in the eye lens substance and/or the cornea substance such that the refractive index and/or the transmission properties for visible useful radiation can be changed to pre-defined parameters, resulting in a defect-reduced vision.

21 Claims, 6 Drawing Sheets

Zur Cornea ← → Zur Netzhaut

METHOD AND APPARATUS FOR ILLUMINATION OF THE EYE

This application claims the benefit of provisional application 60/152,271, filed on Sep. 3, 1999.

DESCRIPTION

1. Field of the Invention

The invention relates to a method and apparatus to allow irradiation of the eye for use in ophthalmology, refractive surgery and laser medicine.

2. Description of the Background Art

For our environment to be seen correctly, its optical image must be faultlessly projected onto the retina of the eye, and the individual surface curvatures and refractive index transitions of the eye must fit the spatial arrangement of receptors in the retina.

Where this faultless optical imaging is disrupted, existing visual deficiencies can be corrected traditionally with the help of glasses. A curved glass with specific refractive index, thickness and curvature relationships is then placed at a defined distance in front of the eye.

It is also known that relatively thin lenses, referred to as "contact lenses", can be put directly onto the eye's cornea.

Apart from these corrections using auxiliary optical means, there is an option of obtaining changes to the eye itself by the use of surgery.

In cornea surgery, changes are made in cornea thickness by removal of tissue (ablation) or changes in its curvature by way of incision (keratotomy). Plastic cornea shaping represents another possible technique. It is accomplished by thermal interaction (thermokeratoplasty).

Because of its "foremost" position, the cornea is easily accessible for surgical treatment and for this reason appears to be researched intensively.

Laser cornea surgery is described in a multitude of documents, generally as laser ablation, mainly performed with excimer lasers, in other cases as thermal cornea shrinking, to induce a change in the curvature of the optical boundary surface.

An apparatus for ophthalmologic surgery is described in U.S. Pat. No. 4,718,418. It uses a scanned UV laser for controlled ablative photo decomposition of selected cornea areas. Irradiation density and exposure time are controlled in such a way that a desired ablation depth is obtained. Scan movements are appropriately coordinated to accomplish a desired change in surface shaping, which converts the cornea into a corrective lens.

The possibilities for eroding a surface with a laser apparatus, which contains means for selection and control of profile and dimensions of the area to be irradiated, with each laser energy pulse, leaving the beam's energy density unvaried, but varying the dimensions of the exposed area between each two pulses, are described in U.S. Pat. No. 4,941,093.

In U.S. Pat. No. 5,334,190, methods and an apparatus for correction of optical vision defects are described. These use an infra-red radiation source and a focusing element to change the eye's curvature by applying focused infra-red radiation to the collagenous cornea tissue in a controlled manner. This leads to heat-induced shrinking of the collagenous cornea tissue and, hence, to a change in cornea curvature.

U.S. Pat. No. 5,423,801 discusses a method and an arrangement containing a laser and a beam shaping mask to reshape the Bowman's membrane without substantially penetrating into the eye's stroma.

Various possibilities of varying the intensity of a cornea-eroding beam by means of erodable masks with pre-defined eroding resistance or graduated intensity filters, by means of selectively varying apertures or other mechanisms of selectively exposed areas are discussed in U.S. Pat. No. 5,505,723.

In U.S. Pat. No. 5,520,679, a refractive laser surgical method is described. It uses a compact low-priced laser system which integrates a computer-controlled scanner with a non-contact unit to perform both photo ablation and photo coagulation. The base system may incorporate flash lamps, diode-pumped solid state UV lasers (193–215 nm), compact excimer lasers (193 nm), free-running Er:Glass (1.54 microns), Ho:YAG (2.1 microns), q-switched Er:YAG (2.94 microns), multi-wave IR lasers (750–1100 nm) and (2.5–3.2 microns). In terms of the benefits of a non-contact scanning device, compactness, higher precision, reduced cost and greater flexibility are cited. Depending on the required beam overlap, ablation rate and coagulation pattern, the lasers are chosen to provide energies from 10 $\mu$J to 10 mJ with repetition rates between 1 and 10000, pulse lengths from 0.01 nanosecond to several hundred microseconds and spot sizes from 0.05 to 2 mm for use in refractive laser surgery.

Cornea reprofiling with a circular beam of ablative irradiation to correct refractive vision defects is shown in U.S. Pat. No. 5,613,965.

Methods for laser ablation and related devices are described in U.S. Pat. No. 5,624,436 & U.S. Pat. No. 5,637,109 and DE 19752949. They contain a laser beam required to work the object to a desired shape, an optical system to deliver the laser beam to the object to be treated, an aperture to vary the ablation area, a controller device for aperture motion, and a master controller to guide the controller device in shaping a curved surface with a required optical characteristic.

This allows the intensity profiles of excimer laser radiation to be improved for cornea ablation.

The possibility of modifying light beams or laser beams in their intensity distribution, in order to erode surfaces to pre-defined profiles using a rotating mask with one or more apertures, is shown in U.S. Pat. No. 5,651,784.

Devices and methods for laser surgery employing pulsed UV excimer lasers at 193 nm with energy densities above 20 mJ per $cm^2$ and repeat rates as high as 25 pulses per second to direct their radiation through a mask onto the cornea tissue and initiate a process of ablative photo decomposition for the removal of tissue in a specified shape and to a specified depth are described in U.S. Pat. No. 5,711,762 & U.S. Pat. No. 5,735,843.

A possibility for combining competing spherical and cylindrical corrections on the cornea surface with the help of a variable iris aperture and a movable slit for reduction of myopia and astigmatism, is shown in U.S. Pat. No. 5,713,892.

To determine the center point location of the eye's pupil after enlargement, a method and a device is given in U.S. Pat. No. 5,740,803.

Information on how to achieve exact control of the location, and determine the point of interaction of a surgical laser, and the controlling of the cornea profile during ophthalmologic surgery performed by means of an applanator, is contained in U.S. Pat. No. 5,549,632.

A favorably shaped beam profile, achieved with a specifically manufactured membrane which is opaque to laser radiation that has different thicknesses in different positions and is placed between the ablation laser and the cornea for surgical treatment, is represented in U.S. Pat. No. 5,807,379.

In WO 98/19741, a device and a method for thermal laser keratoplasty are outlined. They allow the areas of treatment on the cornea to be scanned to shapes such that regression is diminished. Desired changes in the cornea's refractive power are created through locally selected, oblong, pointed photothermal shrinking patterns in the corneal collagen tissue as a result of laser scanning. The objective is to optimize the stress pattern in the cornea. To serve as surgical lasers, laser diodes featuring absorption lengths from 200 to 800 micrometers in the cornea tissue in a wavelength range of 1.3 to 3.3 micrometers are given as an example.

What all these methods have in common is that they influence the eye's imaging performance by changing the curvature of optical boundary surfaces (cornea).

In DE 41 31 361 C2, an apparatus is described, which contains a UV radiation emitting excimer laser, a device to create a certain radiation pattern, imaging optics and a means for fixing the eye, with UV radiation selected in a wavelength range to be within the cornea's absorption range and with an intensity that absorbed UV radiation can produce irreversible changes in the chemical structures in the cornea, thus allowing variation of the refractive index for visible radiation, but not allowing cornea tissue to be removed, and further that the device creating the radiation pattern accomplishes a position-dependent exposure of the cornea to UV radiation, which makes it possible to vary the refractive index depending on position. In addition, in DE 41 31 361 C2 it is reported that excimer lasers with their short wavelengths are able to break up chemical combinations.

High-energy ultra-violet radiation is known to imply a high mutagenic risk, particularly in the spectral range from 240 nm to 280 nm, which is due to resonant absorptions in RNA and DNA.

BRIEF SUMMARY OF THE INVENTION

The task of the invention is to create a method and a device to allow vision defects to be corrected with simple means in a reproducible manner without involving any high-energy UV radiation with its inherent mutagenic risk.

A particular advantage of the invention is that it avoids mutagenic risks by exposing the eye lens to controlled therapeutic radiation in the long-wave UV-A range above cornea absorption and/or in the visible and/or the near infra-red wavelength range and/or the cornea in a defined way with treatment radiation above 1.3 micrometers, thus creating photo-induced local irreversible chemical changes in the eye lens's substance and/or the cornea substance such that the refractive index and/or transmission properties of visible applied radiation is altered according to specified parameters, resulting in an essentially reduced vision defect level, where controlled therapeutic irradiation is accomplished through spatial structuring and modulation over time, as well as intensity control. The spatial structuring follows from spatial modulation and optical transformation.

Changes in the refractive index of the various eye lens regions are achieved efficiently and in a simple manner, using a device for irradiation of the eye, which consists of a radiation-emitting light source, means for radiation modulation over time, means for control of the radiation intensity, means for spatial modulation of radiation, optics to transform and shape the radiation as necessary for applying spatially modulated radiation to the eye, means for determining the orientation of the eye lens axis respectively the eye axis, and means for eye fixation and/or eye tracking, where the light source emits radiation that contains wavelengths for the treatment of the eye lens in the long-wave UV-A range above cornea absorption and/or in the visible and/or near infra-red spectral range and for the treatment of the cornea in the near infra-red spectral range above 1.3 micrometers, which are absorbed in the eye lens and/or the cornea to produce photo-induced chemical alterations in the eye lens's substance and/or the cornea substance, which, if supported by adequate intensity control and radiation modulation over time, causes the eye lens and/or the cornea to change its refractive index for radiation, but causes no strong turbidity in the eye lens region and/or the cornea region due to pure amplitude portions, and further that the means for spatial modulation of radiation which is emitted by the light source are capable of impressing both a structured phase characteristic and a structured amplitude characteristic, further where the optics for transformation and shaping of radiation have at least one optical axis, and the radiation which is spatially modulated in terms of phase characteristic and amplitude characteristic is transformed into pre-defined segments of the eye lens and/or the cornea, which produces a desired equivalent variation in refractive index and/or transmission of the eye lens and/or of the cornea in terms of amount and spatial structuring.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

On the following pages, the invention will be explained in more detail using examples of the embodiments that are at least partially shown in the drawings which are given by way of illustration only, and thus are not limitative of the present invention, and wherein.

FIG. 4A Top view of a simple structure of refractive index variations in plane DD of the eye lens.

FIG. 4B Top view of a simple structure of refractive index variations in plane QQ of the cornea.

FIG. 5A Top view of an irregular structure of refractive index variations in plane FF of the eye lens.

FIG. 5B Top view of an irregular structure of refractive index variations in plane PP of the cornea.

DETAILED DESCRIPTION OF THE INVENTION

Figure 1:
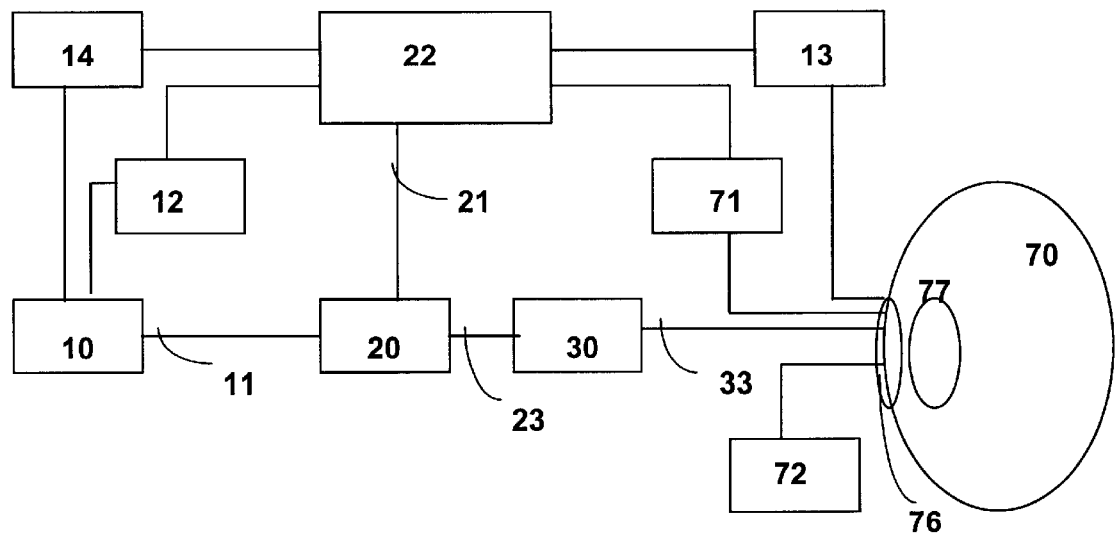
FIG. 1 Principal diagram of the device according to the invention.

As depicted in FIG. 1, the device according to the invention consists of a light source 10 which emits therapeutic radiation 11 for the radiation of the eye lens at any wavelength which is clearly above the operating wavelength of excimer lasers, advantageously greater than 600 nm, and for the radiation of the cornea with a wavelength, which is above a near infra-red wavelength of 1.3 micrometers. It is configured with means for modulation over time 12, means for determining the required and permissible exposure settings 13, for example, by measurement of backscatter from an angled pilot beam, and means for intensity control 14, further including means for spatial modulation 20 of therapeutic radiation 11 to convert electronic signals 21 or signal chains which are advantageously generated in a computer 22 into at least one-dimensional optical structures 23 which may have a phase characteristic and an amplitude characteristic, optics 30 with at least one optical axis 33 for beam shaping and transforming the optical structures 23 to their place of application in eye lens 77 and/or the cornea 76, a device to determine the orientation 71 of the eye axis in relation to the main axis of the optics 30 and means 72 for fixation of the eyeball 70.

Figure 2:
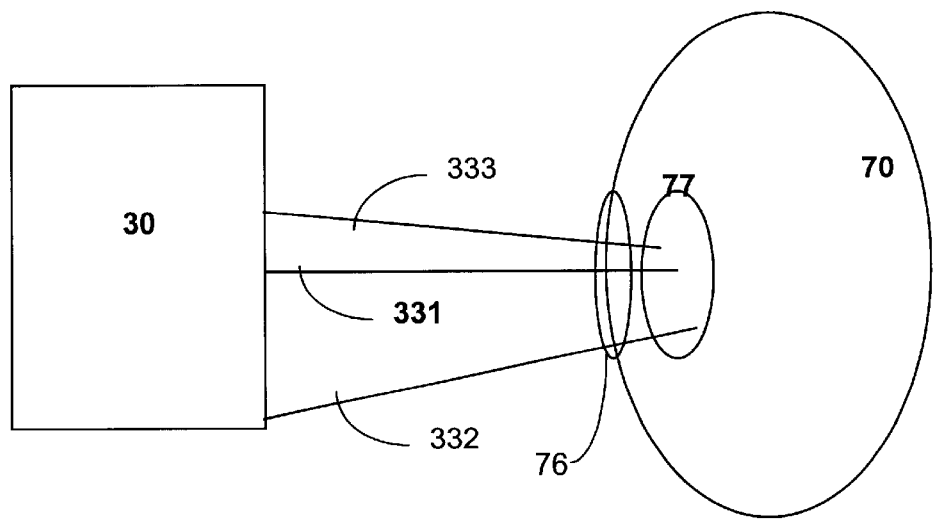
FIG. 2 Embodiment of a detail from FIG. 1 with several optical axes.

FIG. 2. shows an advantageous embodiment of a detail from FIG. 1, in which the "at least one optical axis" consists of the three optical axes 331, 332, 333, with optical axis 331 functioning as the main optical axis. In this embodiment, transformation into pre-defined areas of the eye lens and/or the cornea can be accomplished by superposition of more than one beam, i.e. equivalent to at least one optical axis. Spatial modulations may be different in the various partial beam paths.

The following sections explain the principal procedural methods using three selected examples.

EXAMPLE 1

For a vision defect, basically the amount and azimuthal distribution are known.

These provide the initial data for performing (back) transformation to calculate a complex refractive index distribution (phase and amplitude components) which the lens of the eye and/or the cornea must have if a given refractive defect is to be corrected.

Depending on how fine a structure is required and to what depth the refractive index must be modulated, the right type of optical system can be selected (simple transformation of radiation with the help of one optical axis or superposition of radiation over more than one optical axis, in other words: from a simple flat image projection to coherent multiple beam superposition).

The concrete wavelength of radiation and its coherence properties can be specified depending on the desired structure of refractive indexes.

The power range and timing specifications of the light source (pulse duration, pulse frequency, pulse number) can also be selected. Selection of application parameters must ensure that a "total cataract" is prevented.

From the required structure of refractive indexes, computer technology then determines the particular spatially modulated radiation structure which, interacting with a particular transformation and beam formation optics is best suited to achieve this refractive index structure in the eye lens and/or the cornea. As part of the procedure, it may prove advantageous to create very distinct amplitude changes in some areas of the eye lens and/or the cornea, which do exhibit cataract-like features respectively represent a slight interstitial corneal haze , but lead to enhanced eye vision by mutual interaction of the entire structure in the eye lens and/or the cornea. Such improvements outweigh slight losses in transmission.

Spatial modulation can be performed with electro-optical converters in transmission or reflection mode, or using a scanner. It can be based on different coordinate grids, for example, Cartesian or polar.

Once the structure is created in the eye lens and/or the cornea, it acts as a complex diffractive imaging structure (for example, through its predominant) phase portions (refractive index variations) and also with its (partially present) amplitude portions (transmission variations), which improves the refractive power in the eye in such a way that fault-corrected vision becomes possible.

In addition, those types of structures can be implemented that provide optimized vision during accommodation movements of the eye over a greater range of accommodation.

EXAMPLE 2

The vision defect of an eye is again known with its amount and azimuthal distribution of discrepancies in refractive power. These values are determined in the traditional way. It is useful to know the eye's inner refractive power structure in a very fine grid (much smaller than 0.1 mm).

In addition, it is very useful to have knowledge of the changes in defective vision over a reasonable period in the past.

Depending on the amount of ametropia and the rate of change (relative stability or drastic changes within a certain period of time), a decision has to be made regarding the basic applicability of this method. It should not be used if the refractive power is found to have changed considerably within a short time (e.g. by more than 2 diopters in the course of one year). This has to be taken into consideration because corrections, once implemented, will have a pronounced long-term stability.

The method is very well suited where there is strong or highly irregular variance over the azimuth or over the distance from the vision axis. The more complicated the refractive index structure, the better are the prospects for successful application of the method.

The method is also very well suited in cases when visual acuity is to be improved, particularly for conditions with low light (e.g. in the evening, at night, night driving, inside dark rooms) or illumination with predominantly long-wave radiation (warm light illumination).

The method is non-invasive, it implies no risk of infection, no mutagenic risk due to high-energy radiation, and it can be practiced under outpatient conditions.

Depending on the amount of necessary correction in refractive power, a decision is made on whether the method is to be applied as a pure projection method along an optical axis 33 (see FIG. 1.)or as a coherent optical superposition method with more than one optical axis 331, 332, 333 (see FIG. 2). The latter needs to be selected if a major change is to be achieved in refractive power. In this case, the required refractive index variations have to be created in microscopically small dimensions (about 1 micron/micrometer or even less).

Data on the wavelengths and angle ranges for which a given correction is to be optimally matched, can be derived from the individual indication. This decision has an impact on the light source wavelength to be chosen for treatment.

The time specifications of therapeutic exposure (cw, qcw or pulse mode, pulse duration and repeat frequency) must be selected in accordance with the examinations to be specified for each individual application.

Pulse modes with frequencies near the kilohertz range and pulse durations from some microseconds to some milliseconds have been successfully used.

Figure 4A:
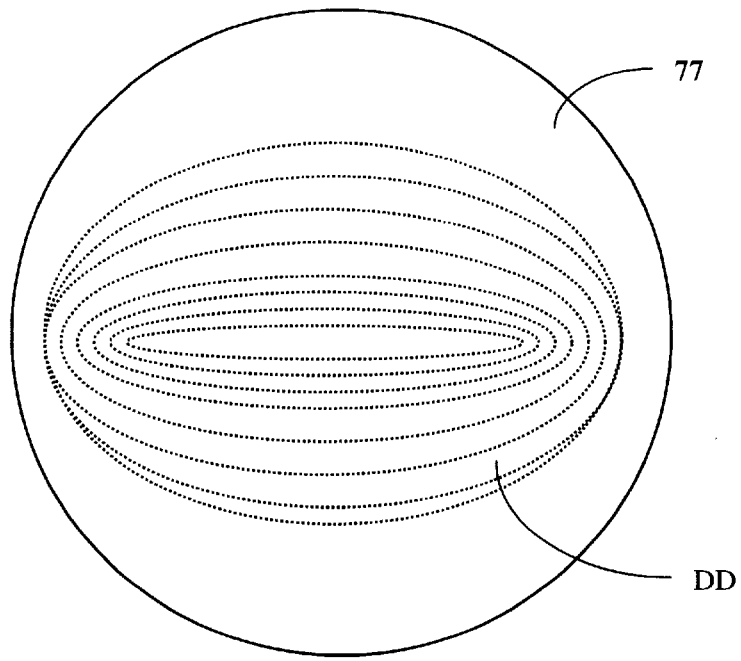
Figure 4B:
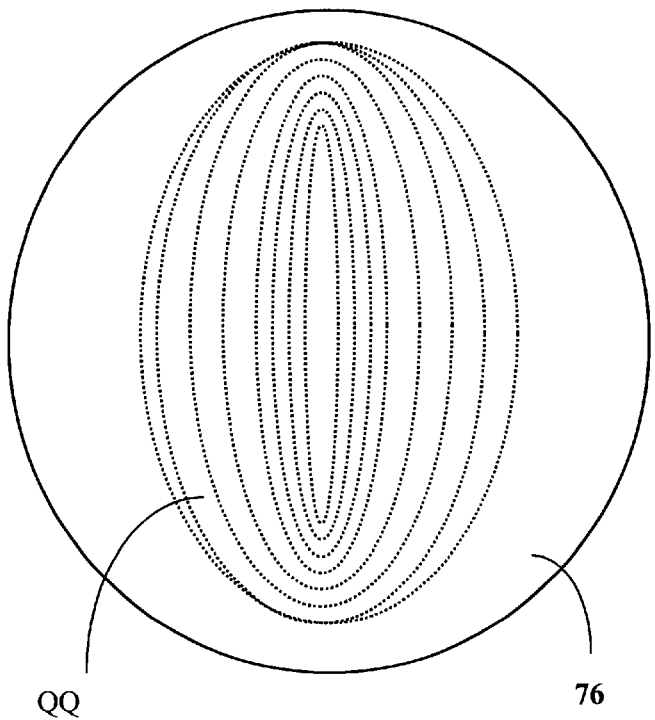
Figure 5A:
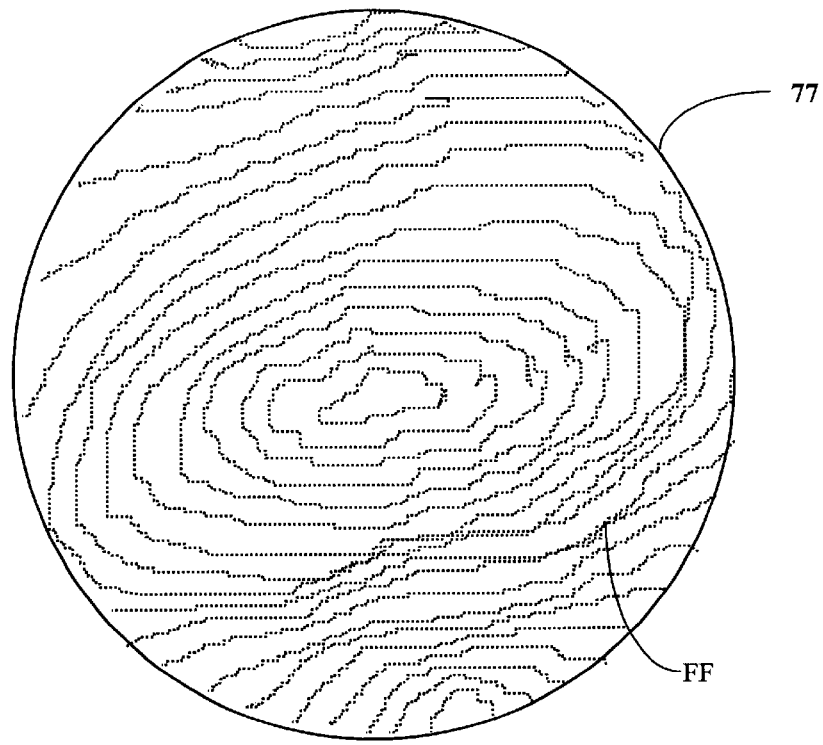
Figure 5B:
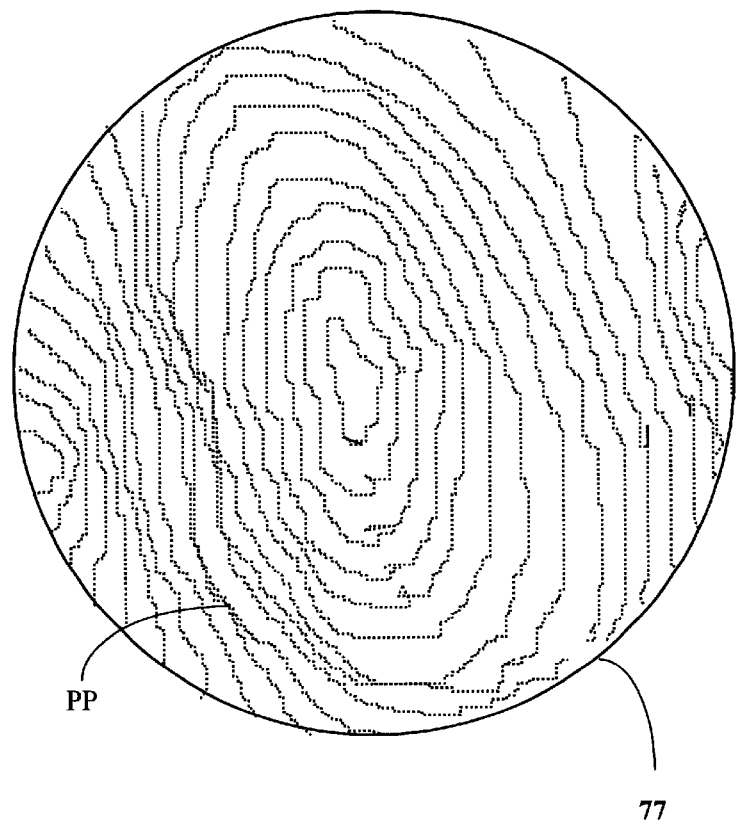
Figure 6A:
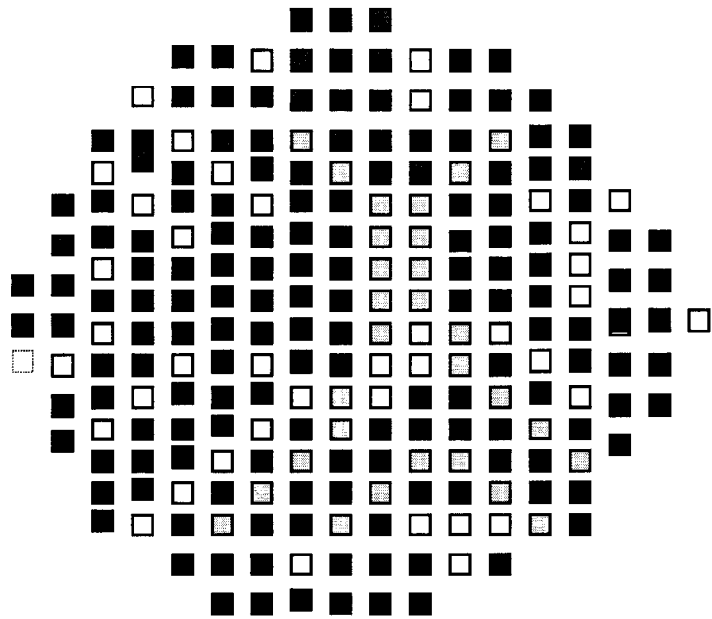
FIG. 6A Two-dimensional optical structure with amplitude and/or phase characteristic in the mask plane to create refractive index variations in plane GG of the eye lens, where different amplitudes are represented by gray values, and phase portions appear as dotted lines.
Figure 6B:
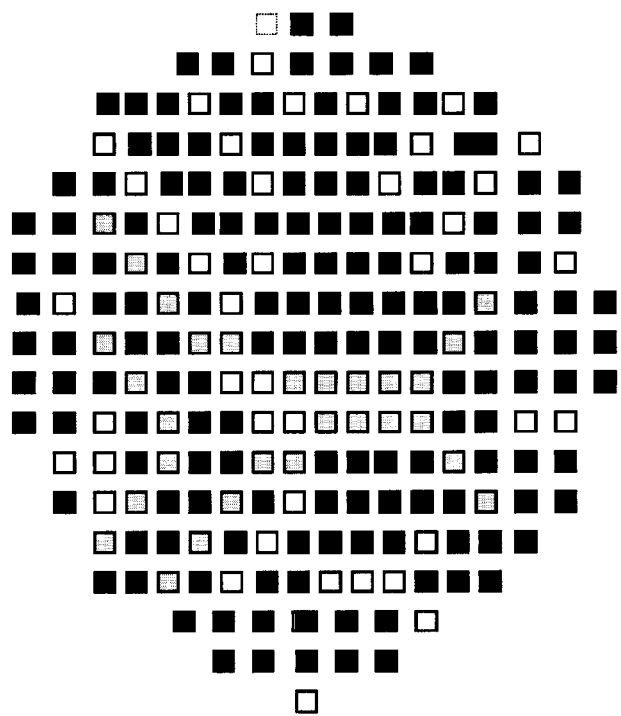
FIG. 6B Two-dimensional optical structure with amplitude respectively phase characteristics in the mask-plane to create refractive index variations in plane JM of the cornea, whereas different amplitudes are represented by gray values, and phase portions appear as dotted line.

Suitable optics can be selected based on the required change in refractive power, the light source's wavelength, and the decision for projection or superposition. Once the optics are defined, the type of spatial modulation 20 can be determined (a possible example of such a "template" is shown in the FIGS. 6A and 6B) by way of calculation. After optical transformation, the spatial modulation leaves intensity structures behind in eye lens 77 and/or the cornea 76, which in conjunction with the pre-selected exposure time settings, create the desired equivalent spatial distribution of a refractive index structure. Such conceivable intensity or refractive index structures can be seen in FIGS. 4A, 4B and 5A, 5B. FIGS. 4A, 4B concern a simple case, FIGS. 5A, 5B a somewhat more irregular case. The spacings within a given structure may vary, they may be small or of a larger size, they may increase or decrease or alternate in one direction. The resulting azimuthal orientation of a structure may contain any angle in keeping with the correction requirements. Smaller spacings in a structure are equivalent to stronger changes in the direction of light beams, i.e. to stronger refractive power. According to the laws of optical diffraction, deflection occurs in a direction that is orthogonal to the structural expansions.

Figure 3A:
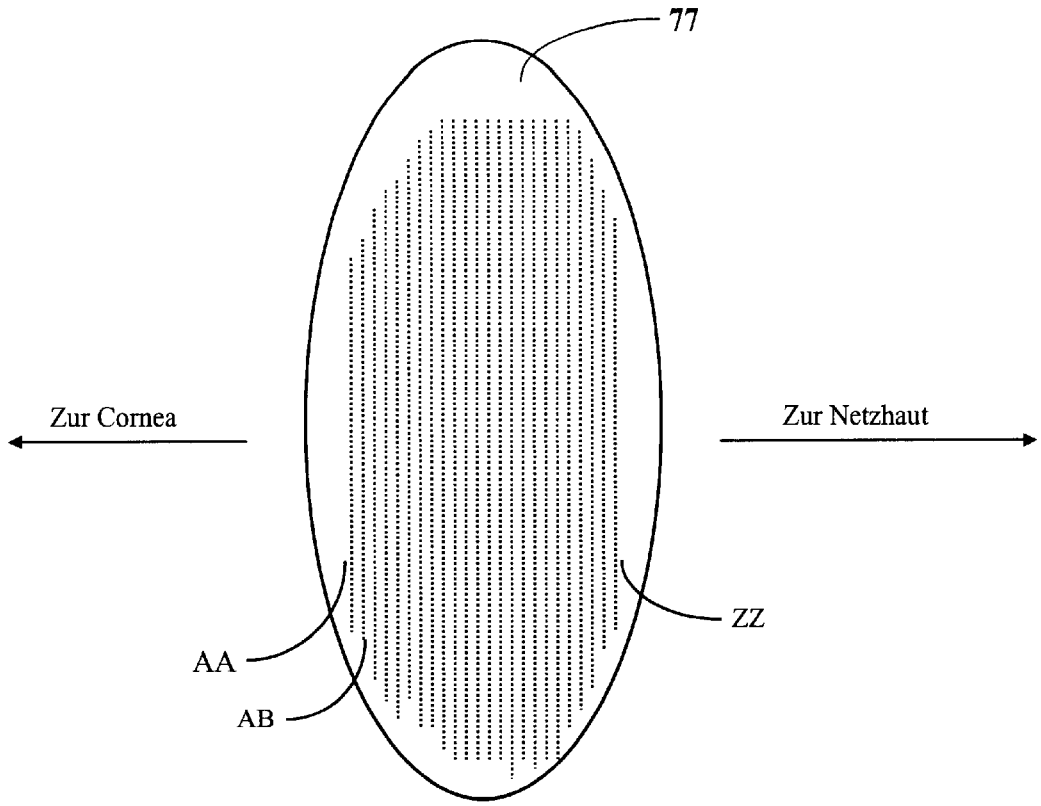
FIG. 3A A cross section of the eye lens with different planes of refractive index variations (AA to ZZ).
Figure 3B:
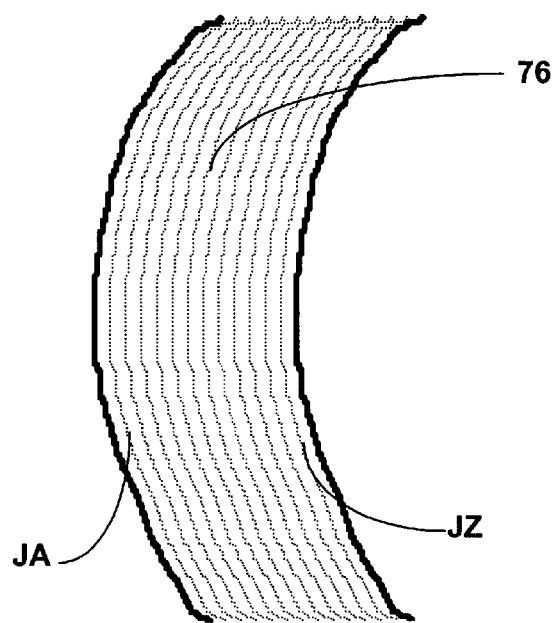
FIG. 3B A cross section of the cornea with different planes of refractive index variations JA to JZ.

To ensure an efficient correction in refractive power, several, to many, such refractive index structures have to be created in a graduated pattern over the depth of the eye lens and/or the cornea. This can be seen in schematic cross sections in FIGS. 3A and 3B.

EXAMPLE 3

Figure 7:
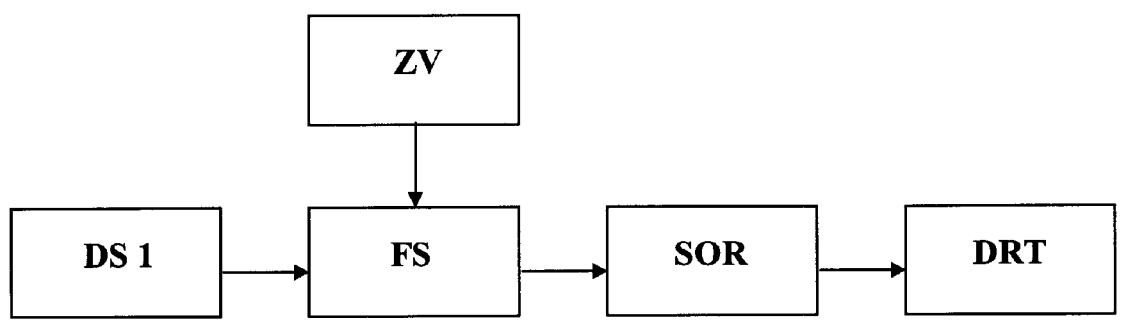
FIG. 7 Schematic of compiling "data sets after back transformation" by "simulated optical back transformation" of the "areola model of necessary changes in refractive power" to "target specifications for refractive power structure after correction", and "data sets of the refractive power structure in the eye to be treated".

The eye to be treated is examined. By arranging a very close-meshed two-dimensional grid in parallel with the eye lens plane and/or the cornea plane, the distribution of the eye's refractive power (not only that of the lens and/or the cornea, but the entire optical path in the eye) is determined. As a result, an initial data set DS1 on the condition of refractive power distribution in the eye is obtained (e.g. in a computer) (see diagram in FIG. 7). The situation to be corrected can be analyzed more exactly, if the refractive power structure is determined not only in, or parallel to, the optical axis, but also at different angles to the optical axis.

From the difference between a mapped actual situation chart (DS1) and the target specifications (ZV) (defining a desired refractive power after correction), an areal model (FS) is obtained. DS1 is a data set containing refractive power distribution for the eye being treated. ZV are target specifications for refractive power distribution after correction. FS is an areal model for changes necessary in refractive power. It described the changes in refractive power necessary for specific subareas of the eye-lens and/or the cornea. These subareas can be very small. With strongly irregular refractive power structures, they must even be very small compared to the eye lens' size and/or the cornea's size. For higher accuracy of the examination results, several areal models (FS) should be recorded at different angles to the optical axis.

The areal model(FS) then undergoes a simulated optical back transformation (SOR) in a computer. This requires certain specifications to be made for the device which is to be selected for performing the correction method according to the invention (selections for optics, wavelength emitted by light source, number of points in areal model FS and means for spatial modulation 20).

Simulated optical back transformation (SOR) is an iterative process.

Back transformation delivers a group of data sets (DRT). Each data set is intended for creating a structure of refractive index variations in one of the various layers (AA to ZZ) of the eye lens (see FIG. 3A)and/or JA to JZ of the cornea (see FIG. 3B).

For a given selected eye treatment procedure to be operational, the corresponding data sets must be available in a computer 22 in post-transformation state (DRT). They are converted into chains of electronic signals 21 which use radiation 11 from a light source 10 to create several, at least one-dimensional, optical structures 23 in the means for spatial modulation 20 of therapeutic radiation which may have an phase or/and a amplitude characteristic. The latter is modulated over time and controlled in its intensity by computer 22.

The optical structure 23 either passes through optics 30 to be projected into the eye lens 77 and/or the cornea 76, or structures 231, 232, 233 are superimposed on the eye lens 77 and/or the cornea 76 by multi-beam superposition along the subbeams 331, 332, 333.

It is necessary to fix the eye 70 with special means 72. Depending on the eye axis orientation previously determined with means 71, fine corrections in the position of structure 23 can be achieved e.g. by modifying the signal sequence chains 21.

Means 13 are provided for determining the required exposure parameters and possible interactions of previously determined permissible exposure parameters, especially the "distance," to inadmissibly high applied power levels. An advantageous embodiment of means 13 consists of a real time control loop, in which the changes achieved in refractive power and the data from the corresponding areal model (FS) define the control variables.

The invention is not restricted to the embodiment examples discussed herein. Rather, it is possible for the above described means and features to be combined and modified in order to configure further embodiments without leaving the scope of this invention.

What is claimed is:

1. A method to irradiate an eye for correction of vision defects by way of changes in refractive power, the method comprising the step of:

exposing at least one of
the lens of the eye to controlled therapeutic radiation in at least one of long-wave UV-A range above cornea absorption, visible ranges, and near infra-red wavelength ranges, and
the cornea in a defined way with treatment radiation in the near infra-red wavelength range above 1.3 micrometers, whereby local photo-induced irreversible chemical changes in at least one of the eye lens's substance and the cornea substance are created such that at least one of refractive index and transmission properties for visible useful radiation are variable to predefined parameters, resulting in defect-reduction vision.

2. The method according to claim 1, wherein controlled therapeutic irradiation is achieved by spatial and timing modulation in conjunction with intensity control.

3. The method according to claim 2, wherein spatial modulation impresses on the therapeutic radiation both a structured phase characteristic and a structured amplitude characteristic.

4. The method according to claim 2, wherein radiation that is spatially modulated for phase characteristic and amplitude characteristic, is transformed into predefined areas of at least one of the eye lens and cornea, thus creating at least one of a desired equivalent complex variation in the refractive index both in terms of amount and spatial structuring a transmission variation in at least one of the eye lens and cornea, which influences applied radiation incident in real application situations in such a way that an optimized defect-reduced image will emerge.

5. The method according to claim 1, wherein the complex refractive index distribution with phase and amplitude components as required for correction of visual defects is determined by (back) transformation calculations from definable target specifications and the analyzed refractive power distribution.

6. The method according to claim 1, wherein the therapeutic radiation for radiation of the eye lens consists of at least one of laser radiation in the long-wave UV-A range above cornea absorption, in the visible ranges, and the near infra-red ranges, and the treatment radiation for radiation of the cornea consists of laser radiation in the near infra-red range above 1.3 micrometers.

7. The method according to claim 6, wherein laser radiation is emitted either continuously or in timed pulses.

8. The method according to claim 1, wherein at least one of the eye lens content and the respective cornea regions are additionally sensitized to therapeutic radiation.

9. The method according to claim 8, wherein such additional sensitization is achieved through pharmacological measures.

10. The method according to claim 8, wherein such additional sensitization is achieved through biochemical measures.

11. The method according to claim 2, wherein intensity control of therapeutic radiation determines the optimal individual setting for exposure energy, which is accomplished through a pilot beam applying pulsed radiation in a step-by-step procedure onto a marginal area of at least one of the eye lens and cornea to build a trial refractive index variation, which is then verified in terms of amount with the help of optical means.

12. The method according to claim 1, wherein the wavelength of therapeutic radiation for radiation of the eye lens is clearly above the wavelength of excimer lasers and is greater than 600 nm and the wavelength of the treatment radiation for the radiation of the cornea is located in a small spectral range near 1.3 micrometers.

13. The method according to claim 1, wherein aspiration of eye tissue is avoid due to the exposing using controlled therapeutic radiation.

14. A device for irradiation of an eye to correct defects in vision, the device comprising a light source which emits therapeutic radiation, means for timing modulation of the therapeutic radiation, means to control intensity of therapeutic radiation, means for spatial modulation of therapeutic radiation, optics to transform and shape therapeutic radiation in order to bring spatially modulated radiation into the eye, means for determining orientation of an eye lens's axis or eye axis, and means for at least one of fixation and tracking of the eye, wherein the light source emits therapeutic radiation for radiation of and absorption into at least one of the eye lens in at least one of wavelengths in long-wave UV-A range above cornea absorption, visible ranges, and near infrared spectral ranges, and the cornea in wavelengths in the near infra-red spectral range above 1.3 micrometers, where the means for spatial modulation of therapeutic radiation emitted by the light source is capable of impressing both a structured phase characteristic and structured amplitude characteristic on the therapeutic radiation, where the optics for transformation and shaping of radiation ahs at least one optical axis, and where therapeutic radiation which is modulated in terms of phase characteristic and amplitude characteristic is transformed into certain predefined areas of at least one of the eye lens and cornea, thus producing a desired equivalent complex variation of the refractive index in terms of amount and spatial structuring and/or a transmission variation in at least one of the eye lens and cornea, which will influence useful radiation incident in real application situations in such a way that an optimized defect-reduction image occurs in the eye.

15. The device according to claim 14, wherein the means for spatial modulation contains electro-optical converters.

16. The device according to claim 15, wherein the electro-optical converters work in reflection mode.

17. The device according to claim 15, wherein the electro-optical converters work in transmission mode.

18. The device according to claim 14, wherein the means for spatial modulation contains scanners.

19. The device according to claim 14, wherein the optics for transformation of shaping of therapeutic radiation contains scanners.

20. The device according to claim 14, wherein the means for spatial modulation and the optics for beam transformation and shaping interact in such a way that reduced-defect vision becomes possible even with different accommodation states of the eye lens.

21. The device according to claim 14, wherein the light source enables aspiration of eye tissue to be avoided.

* * * * *

UNITED STATES PATENT AND TRADEMARK OFFICE
CERTIFICATE OF CORRECTION

PATENT NO.    : 6,478,792 B1
DATED         : November 12, 2002
INVENTOR(S)   : Hartmut G. Hansel It is certified that error appears in the above-identified patent and that said Letters Patent is hereby corrected as shown below:

<u>Title page,</u>
Item [75], Inventor, please correct the inventor's name from "Harmut G. Hansel" to --Hartmut G. Hansel --.

Signed and Sealed this

Eighth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,478,792 B1
DATED : November 12, 2002
INVENTOR(S) : Hartmut G. Hänsel It is certified that error appears in the above-identified patent and that said Letters Patent is hereby corrected as shown below:

<u>Title page,</u>
Item [75], Inventor, please correct the inventor's name from "Hartmut G. Hansel" to -- Hartmut G. Hänsel --.

Signed and Sealed this

Twenty-first Day of October, 2003

JAMES E. ROGAN
*Director of the United States Patent and Trademark Office*